United States Patent [19]

Chikama

[11] Patent Number: 4,718,407
[45] Date of Patent: Jan. 12, 1988

[54] OPERATING MECHANISM FOR BENDABLE SECTION OF ENDOSCOPE

[75] Inventor: Toshio Chikama, Tokyo, Japan

[73] Assignee: Kabushiki Kaisha Machida Seisakusho, Tokyo, Japan

[21] Appl. No.: 3,859

[22] Filed: Jan. 16, 1987

Related U.S. Application Data

[63] Continuation-in-part of Ser. No. 922,020, Oct. 22, 1986.

[30] Foreign Application Priority Data

Apr. 4, 1986 [JP] Japan ............................ 61-49840[U]

[51] Int. Cl.$^4$ .............................................. A61B 1/00
[52] U.S. Cl. ......................................... 128/4; 138/118
[58] Field of Search ................. 128/4, 6; 138/120, 118

[56] References Cited

U.S. PATENT DOCUMENTS

| | | | |
|---|---|---|---|
| 4,499,895 | 2/1985 | Takayama | 128/6 |
| 4,503,842 | 3/1985 | Takayama | 128/4 |
| 4,559,928 | 12/1985 | Takayama | 128/6 |
| 4,617,914 | 10/1986 | Ueda | 128/4 |
| 4,655,257 | 4/1987 | Iwashita | 128/4 X |
| 4,659,195 | 4/1987 | D'Amelio et al. | 128/4 X |

Primary Examiner—William H. Grieb
Attorney, Agent, or Firm—Kane, Dalsimer et al.

[57] ABSTRACT

An endoscope comprises an operating body and an inserting portion extending therefrom. A distal end section of the inserting portion is formed into a resiliently bendable section. An angularly movable member is mounted within the operating body for angular movement around a center of rotation. The bendable section is operatively connected to the angularly movable member through a pair of operating wire sections. An operating member located exteriorly of the operating body is operatively connected to the angularly movable member. A biasing mechanism is associated with the operating body and includes a spring spirally wound within a casing. One end of the spring drawn out of the casing applies a spring force to a point of action on the angularly movable member spaced from the center of rotation thereof. When the bendable section extends straight, the spring force of the spring passes through the center of rotation so as to apply substantially no moment of rotation to the angularly movable member, and when the bendable section is bent, the spring force of the spring applies moment of rotation to the angularly movable member.

15 Claims, 8 Drawing Figures

OPERATING MECHANISM FOR BENDABLE SECTION OF ENDOSCOPE

This application is a continuation-in-part of application Ser. No. 922,020 filed Oct. 22, 1986.

BACKGROUND OF THE INVENTION

The present invention relates to an endoscope comprising an inserting portion insertable into, for example, a body cavity of a subject, an interior of a machine, or the like, to perform observation and, more particularly, to an operating mechanism for a resiliently bendable section of the inserting portion.

A usual, conventional endoscope comprises an operating body and an inserting portion extending therefrom. The inserting portion has a distal end section formed into a resiliently bendable section. An angularly movable member such as pulley or the like is mounted, within the operating body, on a shaft for angular movement therewith around an axis thereof. An operating member such as lever is connected to an end of the shaft which projects outwardly from the operating body. The angularly movable member is operatively connected to a distal end of the bendable section through a pair of operating wire sections.

An operator or operating surgeon inserts the inserting portion of the endoscope into, for example, a body cavity of a subject and, thereafter, he turns the operating lever to angularly move the angularly movable member around the axis of the shaft. The angular movement of the angularly movable member is transmitted to the bendable section through the operating wire sections to bend the bendable section toward any desired direction.

As the bending angle of the bendable section increases, the restoring force of the bendable section tending to return to its original straight condition increases. However, since the operating surgeon turns the operating member with his hand gripping the operating body, he cannot apply his so great turning force to the operating member. Consequently, it is difficult for the operating surgeon to greatly bend the bendable section against the restoring force thereof.

As disclosed in Japanese Patent Publication No. 56-13455 and Japanese Utility Model Application Laid-Open No. 58-160002, an arrangement has been proposed in which an electric motor is used as a power source and is directly connected to the shaft of the angularly movable member. With such arrangement, however, it is required for the motor to be rotated at low speed and to output high torque. Thus, the endoscope is increased in overall dimension and is also increased in weight, so that the operability of the endoscope is reduced.

In order to eliminate the above disadvantage, a construction has been proposed in which a small electric motor is used in combination with a gear train having high reduction ratio, to obtain high torque within a low rotational speed range of the motor.

With the construction described above, in the event that the failure of electric power supply, malfunction or the like occurs and it becomes necessary to manually operate the endoscope, force must be transmitted in the direction opposite the usual direction, that is, the operating surgeon has to operate the operating member to angularly move the angularly movable member, to thereby rotate the motor. However, since the gear train is used which has a high reduction ratio, the power transmitting ratio of the gear train is low. In addition, magnetic force acts between rotor and stator of the motor. Accordingly, it is not easy for the operating surgeon to rotate the motor. This renders it considerably difficult for the operating surgeon to manually operate the endoscope.

In particular, in the event that the failure of electric power supply occurs after the inserting portion has been inserted into the body cavity of the subject and the bendable section has been bent to a desired angle, it might be no longer possible to withdraw the inserting portion out of the cavity of the subject, because it is impossible to release the bent condition of the bendable section.

OBJECT AND SUMMARY OF THE INVENTION

An object of the present invention is to provide an endoscope which has an improved operability.

According to the invention, there is provided an endoscope comprising:

an operating body;

an inserting portion extending from the operating body and having a distal end section formed into a resiliently bendable section;

an angularly movable member mounted within the operating body for angular movement around a center of rotation;

a pair of operating wire means having their respective one ends operatively connected to the angularly movable member and the respective other ends operatively connected to the bendable section;

an operating member arranged exteriorly of the operating body and operatively connected to the angularly movable member, for angularly moving the angularly movable member to resiliently bend the bendable section; and a biasing mechanism associated with the operating body and operatively connected to the angularly movable member, said biasing mechanism including a casing and strap-like spring means spirally wound within the casing, the spring means having one end thereof drawn out of the casing and the other end located within the casing, the spring means applying a spring force to a point of action on the angularly movable member spaced from the center of rotation thereof in such a manner that when the bendable section extends straight, the spring force of the spring means passes through the center of rotation of the angularly movable member so as to apply substantially no moment of rotation to the angularly movable member, and when the bendable section is resiliently bent, the spring force of the spring means applies moment of rotation to the angularly movable member.

DETAILED DESCRIPTION

Various embodiments of the invention will now be described with reference to the accompanying drawings.

Figure 1:
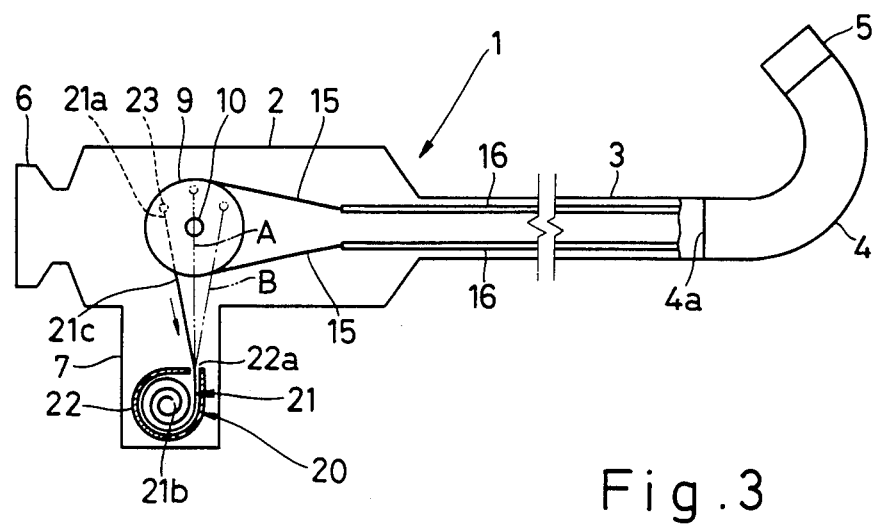
FIG. 1 is a cross-sectional, schematic side elevational view showing an endoscope in accordance with a first embodiment of the invention, in which a pulling force or tension is applied by a biasing mechanism to a pulley.
Figure 2:
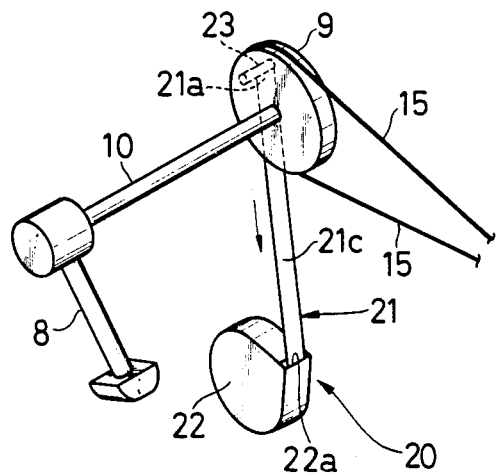
FIG. 2 is a fragmental perspective view showing, on an enlarged scale, the biasing mechanism schematically illustrated in FIG. 1.

Referring first to FIGS. 1 and 2, an endoscope 1 in accordance with a first embodiment of the invention comprises an operating body 2, and a flexible inserting portion 3 extending from a forward end of the operating body 2. The inserting portion 3 has a distal end section formed into a resiliently bendable section 4 which has at its distal end hard or rigid tip component 5. An ocular portion 6 is provided at a rear end of the operating body 2, and a grip portion 7 is provided at a lower side of the operating body 2 and projects therefrom outwardly such that a longitudinal axis of the grip portion 7 intersects an extended line of the inserting portion 3.

The tip component 5 is provided in an end face thereof with a viewing window and an illuminating window. The viewing window is optically connected to the ocular portion 6 through lenses and an optical fiber bundle. The illuminating window is optically connected to a light source unit (not shown) through another optical fiber bundle which extends through the inserting portion 3, the operating body 2 and a guide cable (not shown) connected to the operating body 2.

An operating lever 8 (FIG. 2) serving as an operating member is mounted exteriorly of the operating body 2. A pulley 9 serving as an angularly movable member is mounted within the operating body 2 for angular movement around a center of rotation which is located on the extended line of the inserting portion 3 and which extends perpendicularly thereto. These operating lever 8 and pulley 9 are connected to each other by a shaft 10 having an axis thereof coincident with the center of rotation of the pulley 9. The shaft 10 has one end thereof projecting outwardly from the operating body 2, and the operating lever 8 is fixedly connected to the projecting one end of the shaft 10.

A single continuous wire has a longitudinally intermediate portion thereof which is trained around the pulley 9 and which is fixedly secured thereto at a single point, so that a pair of operating wire sections 15 and 15 extend respectively from upper and lower sides of the pulley 9 toward the inserting portion 3. The pair of operating wire sections 15 and 15 extend respectively through a pair of helical tubes 16 and 16 within the inserting portion 3. Each helical tube 16 has one end thereof fixedly secured to the operating body 2 and the other end fixedly secured to an end 4a of the bendable section 4 opposite to the tip component 5. Ends of the respective operating wire sections 15 and 15 remote from the pulley 9 are fixedly connected to the tip component 5 at respective locations diametrically opposite to each other, i.e., spaced apart from each other through 180 degrees.

A biasing mechanism 20 is arranged within the grip portion 7, and comprises a strap-like or leaf spring 21 having a habit of being spirally wound and casing 22 fixed within the grip portion 7. The spirally wound leaf spring 21 is housed within the casing 22. The leaf spring 21 has one end 21a thereof which is drawn out of the casing 22 through an opening 22a formed therein and which is pivotally connected to the pulley 9 at a location spaced from the shaft 10 by means of a pin 23 serving as a point of action on which the spring force of the leaf spring 21 acts as will be described later. Hereinafter, the end 21a is referred to as "outer end". The leaf spring 21 has the other end 21b (hereinafter referred to as "inner end") which is free and is located within the casing 22.

With the construction described above, since the leaf spring 21 has a habit of being spirally wound, a force acts on a portion 21c (hereinafter referred to as "drawn-out portion") of the leaf spring 21 extending from the opening 22a in the casing 22 to the outer end 21a so as to tend to return the drawn-out portion 21c to its original, spirally wound form. In other words, a force acts to pull the outer end 21a toward the casing 22. The pulling force is substantially constant irrespective of the length of the drawn-out portion 21c, if the entire length of the leaf spring 21 is sufficiently long. In particular, in order to approach the pulling force to a constant value, it is desirable that the inner end 21a is not fixed within the casing 22, but is free. This characteristic of the leaf spring 21 wound spirally is remarkably different from that of a usual coil spring in which its resilient force considerably varies depending upon change in length.

When the bendable section 4 extends straight, the drawn-out portion 21c of the leaf spring 21 passes through the shaft 10, i.e., the center of rotation of the pulley 9 as indicated by the two-dot-and-dash lines A in FIG. 1 and, therefore, the pulling force of the leaf spring 21 also passes through the shaft 10, so that no moment of rotation is applied to the pulley 9.

If it is desired to bend the bendable section 4 in the counterclockwise direction as viewed in FIG. 1, an operator or operating surgeon turns the operating lever 8 in the counterclockwise direction to angularly move the pulley 9 in the same direction around the axis of the shaft 10. At this time, since the pulling force is applied to the pulley 9 as described above, the operating surgeon can turn the operating lever 8 with his small force without difficulty with the aid of the pulling force.

More specifically, as the bendable section 4 is bent and the bending angle thereof increases, the reaction force from the bendable section 4 also increases. This results in increase in the moment of rotation tending to angularly move the pulley 9 around the axis of the shaft 10 in the direction opposite to the operating direction in which the pulley 9 is angularly moved by the operating lever 8. On the other hand, since the pulling force of the leaf spring 21 is substantially constant and the distance between the drawn-out portion 21c and the center of rotation of the pulley 9 increases with the increase in the angle of the angular movement of the pulley 9, the moment of rotation applied to the pulley 9 by the pulling force of the leaf spring 21 is also increased. Consequently, it is possible for the operating surgeon to angularly move the pulley 9 around the axis of the shaft 10 always with his small force, against the reaction force from the bendable section 4.

The moment of rotation applied to the pulley 9 by the leaf spring 21 is set to a level always lower than the moment of rotation applied to the pulley 9 by the reaction force from the bendable section 4 and, therefore, the pulley 9 is prevented from being self-propelled without operating of the lever 8 in such a direction as to increase the bending angle of the bendable section 4.

In addition, as described above, since the moment of rotation applied to the pulley 9 by the pulling force of the leaf spring 21 reduces the moment of rotation applied to the pulley 9 by the reaction force from the bendable section 4, the operating surgeon can maintain the bendable section 4 at any desired angular position, only if he lightly holds the operating lever 8 with his finger. If the reaction force from the bendable section 4 is great, a frictional force may be selectively applied to the pulley 9 or the like to counteract the reaction force.

If it is desired to return the bendable section 4 from the bent position shown in FIG. 1 to the straight position where the bendable section 4 extends straight, the operating surgeon releases his finger from the operating lever 8 or weakens his operating force on the operating lever 8. Then, the bendable section 4 is returned, under its own reaction force, to the straight position.

If it is desired to bend the bendable section 4 in the clockwise direction as viewed in FIG. 1, the operating surgeon can bend the bendable section 4 with his small force, similarly to the counterclockwise bending of the bendable section 4 described above. The position of the drawn-out portion 21c, when the bendable section 4 is bent in the clockwise direction, is indicated by the two-dot-and-dash lines B in FIG. 1.

When the inserting portion 3 of the endoscope 1 is withdrawn from the body cavity of the subject, the operating surgeon releases his finger from the operating lever 8 and gradually pulls the endoscope 1. Then, the bendable section 4 is withdrawn while being bent along the configuration within the body cavity. When the bendable section 4 abuts against the inner wall of the body cavity and is bent thereby, the bendable section 4 is bent with the aid of the force of the leaf spring 21. Thus, the reaction force from the bendable section 4 applied to the inner wall of the body cavity is reduced, making it possible to lighten a burden on the patient.

Figure 3:
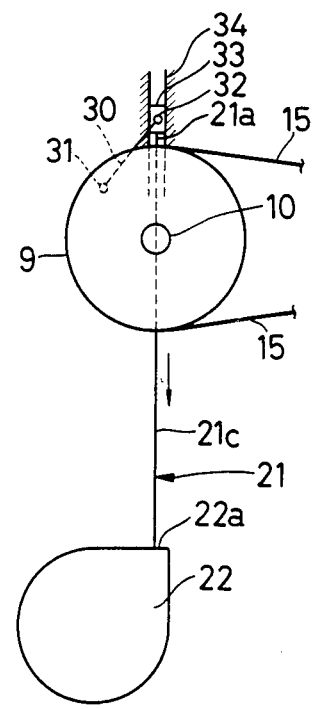
FIG. 3 is a fragmental schematic view showing a biasing mechanism of an endoscope in accordance with a second embodiment of the invention.

FIG. 3 shows a second embodiment of the invention. In FIG. 3, the same or like reference numerals are used to designate parts or components corresponding to those shown in FIGS. 1 and 2, and the detailed description of such corresponding parts or components will therefore be omitted to avoid duplication. In the second embodiment a link 30 is interposed between the pulley 9 and the outer end 21a of the leaf spring 21. Specifically, one end of the link 30 is pivotally connected to the pulley 9 through a pin 31 serving as a point of action on which the spring force of the leaf spring 21 acts. The other end of the link 30 is pivotally connected to a slider 33 through a pin 32. The outer end 21a of the leaf spring 21 is connected to the slider 33. The slider 33 is guided by a guide 34 so as to move on a straight line passing through the shaft 10 and the opening 22a in the casing 22. Accordingly, the drawn-out portion 21c of the leaf spring 22 passes always through the shaft 10.

With the construction shown in FIG. 3, the pulling force of the leaf spring 21 acts on the pulley 9 in the longitudinal direction of the link 30. When the bendable section 4 (FIG. 1) extends straight, the extended line of the link 30 passes through the shaft 10 and, accordingly, the pulling force of the leaf spring 21 acting on the pin 31 passes through the shaft 10, so that no moment of rotation is applied to the pulley 9. In the second embodiment, the use of the link 30 makes it possible to abruptly increase the moment of rotation applied to the pulley 9 by the pulling force of the leaf spring 21, as the angle of the angular movement of the pulley 9 increases and exceeds a certain value. Thus, it is possible for the second embodiment to counteract the moment of rotation applied to the pulley 9 by the reaction force from the bendable section 4, the moment of rotation being abruptly increased as the bending angle of the bendable section 4 increases and exceeds a certain value substantially corresponding to the above-noted value.

Figure 4:
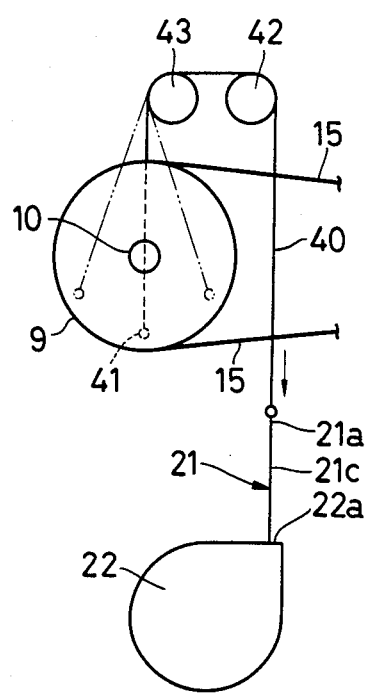
FIG. 4 is a view similar to FIG. 3, but showing a third embodiment of the invention.

FIG. 4 shows a third embodiment of the invention. In FIG. 4, the same reference numerals are used to designate parts or components corresponding to those shown in FIGS. 1 and 2, and the detailed description of such corresponding parts or components will be omitted. In the third embodiment, a wire 40 is used which has one end thereof connected to the outer end 21a of the leaf spring 21, and the other end pivotally connected to the pulley 9 through a pin 41 serving as a point of action. The wire 40 is trained around pulleys 42 and 43.

Figure 5:
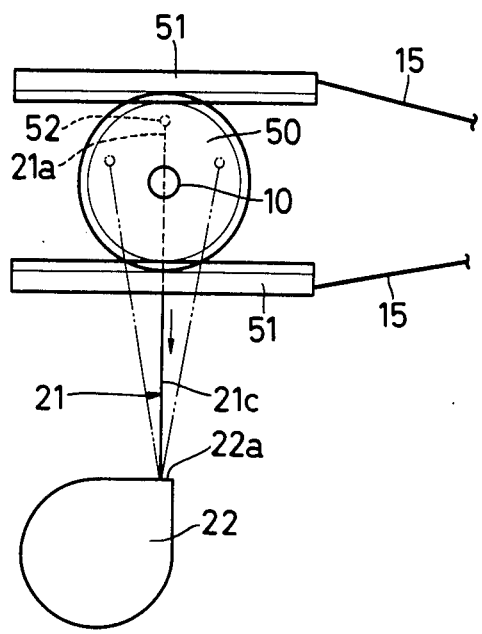
FIG. 5 is a view similar to FIG. 3, but showing a fourth embodiment of the invention.

FIG. 5 shows a fourth embodiment of the invention. In FIG. 5, the same reference numerals are used to designate parts or components corresponding to those shown in FIGS. 1 and 2, and the detailed description of such corresponding parts and components will be omitted. In the fourth embodiment, the angularly movable member is comprised of a pinion gear 50, and the pair of operating wires 15 and 15 are connected respectively to a pair of racks 51 and 51 in mesh with the pinion gear 50. In this embodiment, the outer end 21a of the leaf spring 21 is pivotally connected to a side surface of the pinion gear 50 through a pin 52 serving as a point of action.

Figure 6:
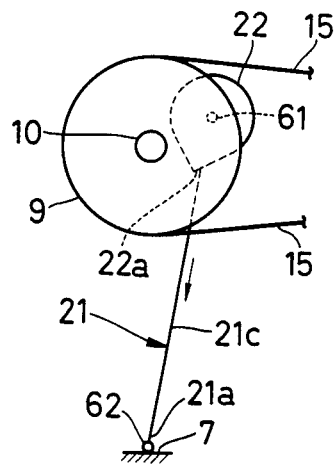
FIG. 6 is a view similar to FIG. 3, but showing a fifth embodiment of the invention.

FIG. 6 shows a fifth embodiment of the invention. In FIG. 6, the same reference numerals are used to designate parts or components corresponding to those shown in FIGS. 1 and 2, and the detailed description of such corresponding parts or components will be omitted. In the fifth embodiment, the casing 22 is pivotally mounted on the pulley 9 through a pin 61 serving as a point of action. The outer end 21a of the leaf spring 21 is pivotally connected to the grip portion 7 through a pin 62.

Figure 7:
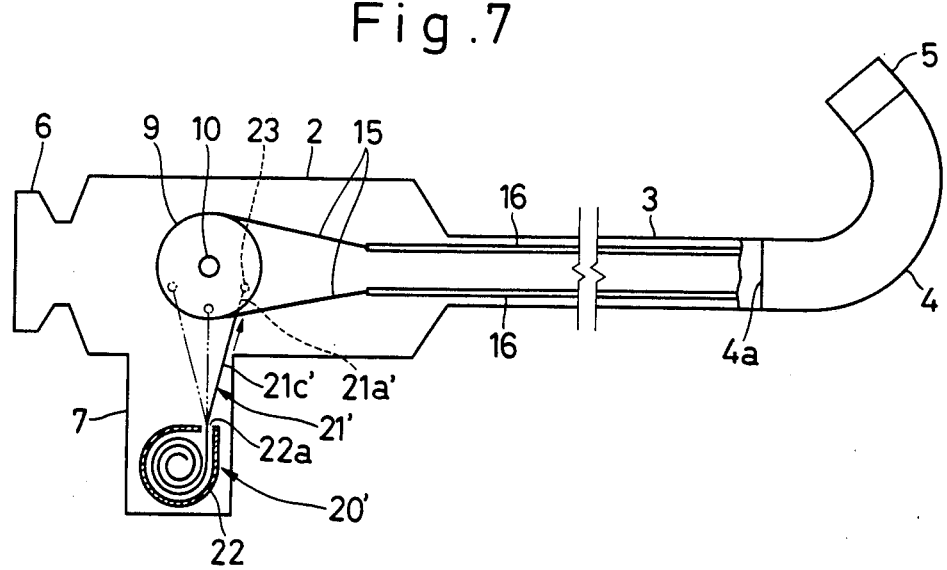
FIG. 7 is a view similar to FIG. 1, but showing an endoscope in accordance with a sixth embodiment of the invention, in which a pushing force is applied by a biasing mechanism to a pulley.

FIG. 7 shows a sixth embodiment of the invention. In FIG. 7, the same reference numerals are used to designate parts or components corresponding to those shown in FIGS. 1 and 2, and the detailed description of such corresponding parts or components will be omitted. In the sixth embodiment, a leaf spring 21' of a biasing mechanism 20' has a habit of extending straight. The leaf spring 21' is forcibly wound spirally and is housed within the casing 22. Accordingly, a portion of the leaf spring 21' wound spirally wihtin the casing 22 tends to extend straight, and a pushing force acts on an outer end 21a' of the leaf spring 21'. The pushing force applies moment of rotation to the pulley 9. When the bendable section 4 extends straight, the extended line of a drawn-out portion 21c' passes through the shaft 10, and the pushing force of the leaf spring 21' also passes through the shaft 10, so that no moment of rotation is applied to the pulley 9 by the pushing force.

Figure 8:
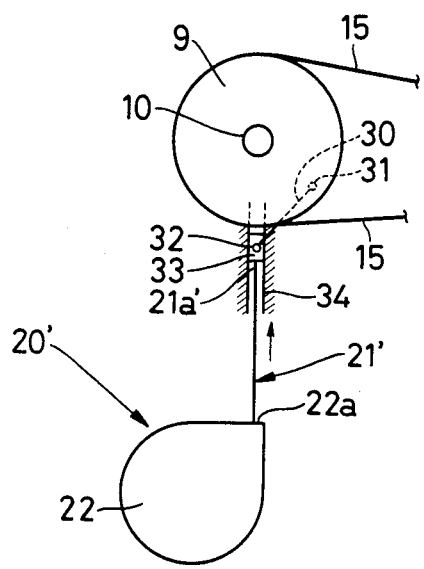
FIG. 8 is a fragmental schematic view showing a biasing mechanism of an endoscope in accordance with a seventh embodiment of the invention.

FIG. 8 shows a seventh embodiment of the invention. In FIG. 8, the same reference numerals are used to designate parts or components corresponding to those shown in FIGS. 1-3 and 7, and the detailed description of such corresponding parts or components will be omitted. The seventh embodiment employs a biasing mechanism 20' identical to that used in the sixth embodiment shown in FIG. 7. The outer end 21a' of the leaf spring 21' is connected to the pulley 9 through the slider 33 and the link 30, similarly to the second embodiment shown in FIG. 3. With such construction, when the bendable section 4 (FIG. 7) extends straight, the pushing force of the leaf spring 21' acting on the pin 31 passes through the shaft 10 and, therefore, no moment of rotation is applied to the pulley 9. The moment of rotation applied to the pulley 9 by the pushing force of the leaf spring 21' abruptly increases as the bending angle of the bendable section 4 increases and exceeds a certain value.

The invention should not be limited to the above-described specific embodiments, but various changes and modifications may be made to the invention. For example, the operating member or lever may be a dial.

The pulley may be connected to the operating member or lever through a gear train. In this case, one of gears forming the gear train serves as the angularly movable member and is biased by the biasing mechanism to indirectly bias the pulley.

The casing of the biasing mechanism may be formed integrally with the operating body.

Although the embodiments of the invention have been described as having the bendable section which is bent in the single plane parallel to the drawing sheets, the bendable section may be bent in two planes perpendicular to each other. In this case, another set of an angularly movable member, an operating member, a pair of operating wire sections and a biasing mechanism is necessary, and the two angularly movable members are biased respectively by the two biasing mechanisms independently of each other.

Although the embodiments of the invention have been described as having the grip portion provided on the lower side of the operating body, such grip portion may dispense with. In this case, the biasing mechanism is located on the extended line of the inserting portion.

As described above, the present invention is arranged such that the moment of rotation applied to the angularly movable member by the force of the spring wound spirally increases with the increase in the bending angle of the bendable section. Accordingly, when it is desired to bend the bendable section, the force required for the operating surgeon or operator to turn the operating member can always be low or small, and it is possible to improve the operability of the endscope.

In addition, it is possible to prevent the inconvenience caused by the failure of electric power supply and the like as is in the motor-driven arrangement.

What is claimed is:

1. An endoscope comprising:
    an operating body;
    an inserting portion extending from said operating body and having a distal end section formed into a resiliently bendable section;
    an angularly movable member mounted within said operating body for angular movement around a center of rotation;
    a pair of operating wire means having their respective one ends operatively connected to said angularly movable member and the respective other ends operatively connected to said bendable section;
    an operating member arranged exteriorly of said operating body and operatively connected to said angularly movable member, for angularly moving said angularly movable member to resiliently bend said bendable section; and
    a biasing mechanism associated with said operating body and operatively connected to said angularly movable member, said biasing mechanism including a casing and strap-like spring means spirally wound within said casing, said spring means having one end thereof drawn out of said casing and the other end located within said casing, said spring means applying a spring force to a point of action on said angularly movable member spaced from the center of rotation thereof is such a manner that when said bendable section extends straight, the spring force of said spring means passes through the center of rotation of said angularly movable member so as to apply substantially no moment of rotation to said angularly movable member, and when said bendable section is resiliently bent, the spring force of said spring means applies moment of rotation to said angularly movable member.

2. An endoscope as defined in claim 1, wherein said other end of said spring means is free so that the spring force of said spring means applied to the point of action on said angularly movable member is substantially constant.

3. An endoscope as defined in claim 1, wherein the moment of rotation applied to said angularly movable member by the spring force of said spring means is always lower than moment of rotation applied to said angularly movable member by a reaction force from said bendable section.

4. An endoscope as defined in claim 1, wherein said spring means has a habit of being spirally wound so that the spring force of said spring means applied to the point of action on said angularly movable member is pulling force.

5. An endoscope as defined in claim 4, wherein said one end of said spring means is pivotally connected to said angularly movable member at said point of action.

6. An endoscope as defined in claim 4, including:
    an opening formed in said casing, said one end of said spring means being drawn out of said casing through said opening;
    a slider to which said one end of said spring means is connected;
    guide means for guiding said slider such that said slider moves on a straight line passing through the center of rotation of said angularly movable member and said opening in said casing; and
    link means having one end thereof pivotally connected to said slider and the other end pivotally connected to said angularly movable member at said point of action.

7. An endoscope as defined in claim 4, including:
    at least one pulley rotatably mounted within said operating body; and
    wire means trained around said pulley, said wire means having one end thereof pivotally connected to said angularly movable member at said point of action and the other end connected to said one end of said spring means.

8. An endoscope as defined in claim 4, including:
    said angularly movable member comprising a pinion gear; and
    a pair of racks in mesh with said pinion gear, the respective one ends of said pair of operating wire means being connected respectively to said pair of racks.

9. An endoscope as defined in claim 4, wherein said casing is pivotally connected to said angularly movable member at said point of action, and said one end of said spring means is pivotally connected to said operating body.

10. An endoscope as defined in claim 1, wherein said spring means has a habit of extending straight and is forcibly wound spirally into said casing so that the spring force of said spring means applied to the point of action on said angularly movable member is a pushing force.

11. An endoscope as defined in claim 10, wherein said one end of said spring means is pivotally connected to said angularly movable member at said point of action.

12. An endoscope defined in claim 10, including:
  an opening formed in said casing, said one end of said spring means being drawn out of said casing through said opening;
  a slider to which said one end of said spring means is connected;
  guide means for guiding said slider such that said slider moves on a straight line passing through the center of rotation of said angularly movable member and said opening in said casing; and
  link means having one end thereof pivotally connected to said slider and the other end pivotally connected to said angularly movable member at said point of action.

13. An endoscope as defined in claim 1, wherein said angularly movable member comprises a pulley, and said pair of operating wire means comprises a single continuous wire trained around said pulley and fixedly secured thereto to form a pair of operating wire sections constituting said pair of operating wire means.

14. An endoscope as defined in claim 1, including:
  a shaft mounted in said operating body for angular movement around the shaft's own axis and having one end projecting outwardly from said operating body, said angularly movable member being mounted, within said operating body, on said shaft for angular movement therewith around said center of rotation coincident with the axis of said shaft, said operating member being connected to the projecting one end of said shaft.

15. An endoscope as defined in claim 1, wherein said operating body has a grip portion having an axis extending in such a direction as to intersect an extended line of said inserting portion, said casing of said biasing mechanism being housed within said grip portion.

* * * * *